(12) United States Patent
Kim et al.

(10) Patent No.: US 10,539,690 B2
(45) Date of Patent: Jan. 21, 2020

(54) X-RAY DETECTOR, X-RAY PHOTOGRAPHING APPARATUS INCLUDING THE SAME, AND METHOD OF MANUFACTURING THE SAME

(71) Applicant: Samsung Electronics Co., Ltd., Suwon-si (KR)

(72) Inventors: Dong-hyuk Kim, Hwaseong-si (KR); Yun-hee Kim, Hwaseong-si (KR); Jea-eun Ryu, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 51 days.

(21) Appl. No.: 16/007,856

(22) Filed: Jun. 13, 2018

(65) Prior Publication Data

US 2018/0356542 A1 Dec. 13, 2018

(30) Foreign Application Priority Data

Jun. 13, 2017 (KR) .......................... 10-2017-0074013

(51) Int. Cl.
  *G01T 1/24* (2006.01)
  *G01T 1/20* (2006.01)
  *A61B 6/03* (2006.01)
  *A61B 6/00* (2006.01)

(52) U.S. Cl.
  CPC ............ *G01T 1/244* (2013.01); *G01T 1/2018* (2013.01); *A61B 6/032* (2013.01); *A61B 6/4208* (2013.01); *A61B 6/502* (2013.01)

(58) Field of Classification Search
  CPC ....... G01T 1/2018; G01T 1/2002; G01T 1/20; G01T 1/2012; G01T 1/24; G01T 1/244; A61B 6/4283; A61B 6/00; A61B 6/4208; A61B 6/484; A61B 6/583; A61B 6/4233; A61B 6/502; A61B 6/032
  USPC ........................................................ 250/366
  See application file for complete search history.

(56) References Cited

U.S. PATENT DOCUMENTS 5,032,732 A * 7/1991 Ito ............................ G21K 4/00
                                                                 250/484.4
5,151,604 A * 9/1992 Kohda ..................... G21K 4/00
                                                                 250/484.4
5,198,685 A * 3/1993 Kitani ............... H01L 27/14665
                                                                    257/433

(Continued)

FOREIGN PATENT DOCUMENTS

JP    2005-043330 A    2/2005
JP    2008-122116 A    5/2008
(Continued)

*Primary Examiner* — Taeho Jo

(57) ABSTRACT

An X-ray detector, an X-ray photographing apparatus including the X-ray detector, and a method of manufacturing the X-ray detector are provided. The X-ray detector includes a photoconversion layer configured to convert an X-ray into light having a wavelength range that is different from a wavelength range of the X-ray, a sensing layer arranged on the photoconversion layer and including a plurality of pixels configured to output the light as an electrical signal, a protective layer arranged on the sensing layer and protecting the sensing layer from physical shocks, and an anti-static layer arranged on the protective layer and preventing an electrostatic charge from being introduced into the sensing layer.

14 Claims, 10 Drawing Sheets

(56) References Cited

U.S. PATENT DOCUMENTS

| | | | |
|---|---|---|---|
| 6,228,286 B1 * | 5/2001 | Leblans | C09K 11/615 250/362 |
| 6,465,794 B1 * | 10/2002 | Suzuki | G21K 4/00 250/484.4 |
| 7,495,226 B2 | 2/2009 | Jadrich et al. | |
| 9,513,380 B2 | 12/2016 | Liu | |
| 9,513,381 B2 | 12/2016 | Jonishi et al. | |
| 2004/0070328 A1 * | 4/2004 | Van Den Bergh | B32B 15/08 313/461 |
| 2005/0258425 A1 * | 11/2005 | Izumi | H01L 27/14665 257/72 |
| 2005/0274916 A1 * | 12/2005 | Shoji | B32B 3/00 250/580 |
| 2006/0033032 A1 * | 2/2006 | Inoue | G01T 1/2018 250/370.11 |
| 2007/0045554 A1 * | 3/2007 | Wakamatsu | G01T 1/2018 250/370.11 |
| 2007/0272873 A1 * | 11/2007 | Jadrich | G01T 1/20 250/370.11 |
| 2009/0061233 A1 * | 3/2009 | Yaegashi | B32B 37/12 428/411.1 |
| 2010/0001198 A1 * | 1/2010 | Yagi | H04N 3/1568 250/370.09 |
| 2010/0116992 A1 * | 5/2010 | Kudo | G21K 4/00 250/361 R |
| 2011/0017912 A1 * | 1/2011 | Goto | C09K 11/628 250/361 R |
| 2011/0017913 A1 * | 1/2011 | Kasai | C09K 11/628 250/361 R |
| 2011/0127439 A1 * | 6/2011 | Imai | H01L 27/307 250/370.08 |
| 2011/0198505 A1 * | 8/2011 | Ishida | G01T 1/202 250/363.01 |
| 2012/0181436 A1 * | 7/2012 | Mollov | G01T 1/2002 250/366 |
| 2012/0256095 A1 * | 10/2012 | Nakatsugawa | H01L 27/14658 250/368 |
| 2013/0099130 A1 * | 4/2013 | Nakahashi | A61B 6/4283 250/394 |
| 2014/0117245 A1 * | 5/2014 | Mollov | G01T 1/2002 250/366 |
| 2014/0239195 A1 * | 8/2014 | Arimoto | C09K 11/55 250/487.1 |
| 2014/0239196 A1 * | 8/2014 | Shoji | G01T 1/202 250/488.1 |
| 2014/0361182 A1 * | 12/2014 | Hasegawa | G01T 1/202 250/367 |
| 2015/0021484 A1 * | 1/2015 | Isa | G01T 1/202 250/361 R |
| 2015/0144889 A1 * | 5/2015 | An | G01T 1/2018 257/40 |
| 2015/0316660 A1 * | 11/2015 | Arimoto | C09K 11/55 250/488.1 |
| 2016/0155526 A1 * | 6/2016 | Arimoto | G21K 4/00 250/488.1 |
| 2016/0216383 A1 * | 7/2016 | Shoji | G01T 1/202 |
| 2016/0260765 A1 * | 9/2016 | Marrs | H01L 29/42356 |
| 2016/0322411 A1 * | 11/2016 | Elen | H01L 27/14623 |

FOREIGN PATENT DOCUMENTS

| | | |
|---|---|---|
| JP | 2010-127680 A | 6/2010 |
| JP | 2011-090024 A | 5/2011 |
| JP | 2011-128000 A | 6/2011 |
| JP | 2014-081363 A | 5/2014 |
| KR | 10-1420250 B1 | 7/2014 |
| KR | 10-2015-0032937 A | 3/2015 |

* cited by examiner

X-RAY DETECTOR, X-RAY PHOTOGRAPHING APPARATUS INCLUDING THE SAME, AND METHOD OF MANUFACTURING THE SAME

CROSS-REFERENCE TO RELATED APPLICATION AND CLAIM OF PRIORITY

This application is based on and claims priority under 35 U.S.C. § 119 to Korean Patent Application No. 10-2017-0074013 filed on Jun. 13, 2017 in the Korean Intellectual Property Office, the disclosure of which is incorporated by reference herein in its entirety.

TECHNICAL FIELD

One or more embodiments relate to an X-ray detector, an X-ray photographing apparatus including the X-ray detector, and a method of manufacturing the X-ray detector.

BACKGROUND

X-ray detectors using a thin film transistor have drawn attention as X-ray detectors which may be used for diagnosis. X-ray detectors output an X-ray image, captured via an X-ray, or an X-ray perspective image as digital signals. The X-ray detectors may be categorized as an X-ray detector using a direct method and an X-ray detector using an indirect method.

The direct method is a method whereby X-rays are directly converted into charges by using a photoconductor, and the indirect method is a method whereby X-rays are converted into visible rays by using a scintillator and the converted visible rays are converted into charges by using a photoelectric conversion device, such as a photodiode.

Recently, wireless X-ray detectors using information technology (IT) are used in a mobile environment, in which users capture images frequently while moving the X-ray detectors, and thus, users frequently drop the X-ray detectors by accident and the X-ray detectors get broken.

SUMMARY

One or more embodiments include an X-ray detector having high durability, an X-ray photographing apparatus including the X-ray detector, and a method of manufacturing the X-ray detector.

One or more embodiments include an X-ray detector capable of removing noise from an image, an X-ray photographing apparatus including the X-ray detector, and a method of manufacturing the X-ray detector.

Additional aspects will be set forth in part in the description which follows and, in part, will be apparent from the description, or may be learned by practice of the presented embodiments.

According to one or more embodiments, an X-ray detector includes a photoconversion layer configured to convert an X-ray into light having a wavelength range that is different from a wavelength range of the X-ray, a sensing layer arranged on the photoconversion layer and comprising a plurality of pixels configured to output the light as an electrical signal, a protective layer arranged on the sensing layer and protecting the sensing layer from physical shocks and an anti-static layer arranged on the protective layer and preventing an electrostatic charge from being introduced into the sensing layer.

Each of the plurality of pixels may include a photodiode and a transistor arranged in parallel in a direction perpendicular to a direction in which the X-ray is incident.

The anti-static layer may be arranged to contact the protective layer.

The anti-static layer may include a conductive material.

The anti-static layer may include at least one of indium tin oxide ITO, indium zinc oxide IZO, a metal, and a conductive organic material.

A thickness of the anti-static layer may range from 50 Å to 500 Å.

The anti-static layer may be grounded.

The protective layer may include at least one of polyimide (PI), polycarbonate (PC), polyethersulfone (PES), polyethylene terephthalate (PET), polyethylenenaphthalate (PEN), polyarylate (PAR), and glass fiber reinforced plastic (FPR).

The X-ray detector may further include a barrier layer arranged at least one of between the photoconversion layer and the sensing layer and between the sensing layer and the protective layer, and preventing water from penetrating into the sensing layer.

The barrier layer may include at least one of silicon oxide SiOx and silicon nitride SiNx.

The X-ray detector may further include a substrate arranged on the protective layer and supporting the protective layer.

The substrate may include glass.

The X-ray detector may further include a first coupling layer configured to couple the substrate and the protective layer together.

The X-ray detector may further include a second coupling layer configured to couple the photoconversion layer and the sensing layer together.

The plurality of pixels may be two-dimensionally arranged.

According to one or more embodiments, an X-ray photographing apparatus includes an X-ray source configured to generate X-rays; and the X-ray detector described above, configured to detect an X-ray which penetrates an object, from among the X-rays generated by the X-ray source.

According to one or more embodiments, a method of manufacturing an X-ray detector includes forming a flexible material layer on a conductive material layer; forming, on the flexible material layer, a sensing layer comprising a plurality of pixels configured to convert light into an electrical signal; and forming, on the sensing layer, a photoconversion layer configured to convert an X-ray into the light, wherein each of the plurality of pixels comprises a photodiode and a transistor arranged in parallel on the flexible material layer.

The method of manufacturing an X-ray detector may further include forming a coupling layer on a substrate and forming the conductive material layer on the coupling layer.

The conductive material layer may be grounded.

The flexible material layer may be formed by a coating process.

The X-ray detector according to the present disclosure may have high durability.

Image noise may be reduced via a structure of the X-ray detector.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
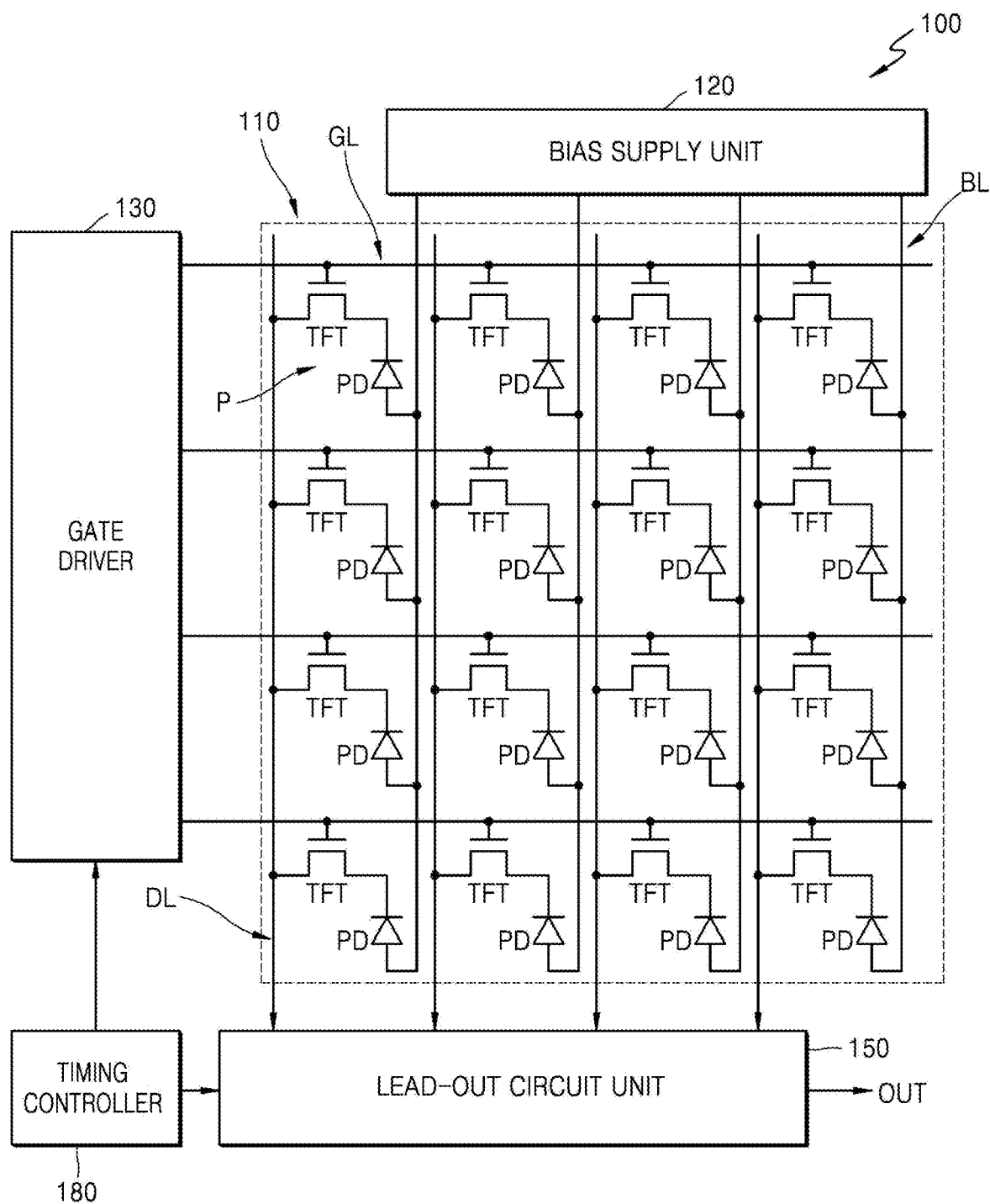
FIG. 1 illustrates, in block diagram format, an X-ray detector according to an embodiment.

FIGS. 1 through 18, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Hereinafter, embodiments of an X-ray detector and an X-ray photographing apparatus including the same will be described in detail with reference to the accompanying drawings, wherein like reference numerals refer to like elements throughout. Repeated descriptions with respect to the like elements will not be given. Expressions such as "at least one of," when preceding a list of elements, modify the entire list of elements and do not modify the individual elements of the list.

In this specification, an "object" may be a human, an animal, or a part of a human or animal. For example, the object may include an organ (for example, the liver, the heart, the womb, the brain, breasts, or the abdomen), blood vessels, or a combination thereof. In addition, throughout the specification, a "user" may be, but is not limited to, a medical expert, for example, a medical doctor, a nurse, a medical laboratory technologist, or a medical imaging expert, or a technician who repairs medical apparatuses.

Hereinafter, when it is described that an object is "above" or "on" another object, it may denote not only that the object is directly above/below/left/right (to) the other object and contacting the other object, but also that the object is above/below/left/right (to) the other object and not contacting the other object. Hereinafter, the present disclosure will be described in detail based on the example embodiments by referring to the accompanying drawings.

FIG. 1 illustrates, in block diagram format, an X-ray detector 100 according to certain embodiments. Referring to the non-limiting example of FIG. 1, the X-ray detector 100 may include a pixel unit 110, a bias supply unit 120, a gate driver 130, a lead-out circuit 150, and a timing controller 180.

The pixel unit 110 may detect an X-ray emitted from an X-ray source (not shown), photoelectrically convert the detected X-ray into an electrical signal, and output the electrical signal. The pixel unit 110 may include a plurality of pixels P arranged in a matrix shape around a region in which a plurality of gate lines GL and a plurality of data lines DL cross each other. The plurality of gate lines GL and the plurality of data lines DL may be arranged to cross each other approximately at right angles. In the illustrative example shown in FIG. 1, 16 pixels P are arranged in 4 rows and 4 columns. However, the present disclosure is not limited thereto, and the number of pixels P may vary.

According to certain embodiments, each of the pixels P includes a photodiode PD detecting an X-ray and outputting a detection signal, for example, a light detection voltage, and at least one switching device configured to transmit the detection signal output from the photodiode PD to a lead-out circuit 150 in response to a request of the gate pulse, wherein the at least one switching device may be, for example, a thin film transistor TFT. Hereinafter, descriptions will be given based on embodiments in which the switching device is the thin film transistor TFT. However, the pixels P are not limited thereto, and may further include a capacitor.

The photodiode PD may detect the X-ray emitted from the X-ray source and output a detected signal as the detection signal. The photodiode PD is a device configured to convert incident light into an electrical detection signal based on a photoelectric effect. For example, the photodiode PD may include a PIN diode.

The bias supply unit 120 may apply a driving voltage to a plurality of bias lines BL. The bias supply unit 120 may apply a certain voltage to the photodiode PD or may selectively apply a reverse bias or a forward bias to the photodiode PD.

The gate driver 130 may sequentially apply gate pluses having a gate-on voltage level to the plurality of gate lines GL. Also, the gate driver 130 may apply reset pulses having a gate-on voltage level to a plurality of reset lines. The gate-on voltage level is a voltage level for turning on transistors of the pixels P. The transistors of the pixels P may be turned-on in response to the gate pulse or the reset pulse.

In response to the gate pulse, the detections signal output from the photodiode PD may be input to the lead-out circuit 150 via the data lines DL. The gate driver 130 may be formed as an integrated circuit (IC) and mounted at a side of a sensing layer (for example, sensing layer 220 in FIG. 2) or formed on the same substrate as a sensing layer 220 by using a thin film process.

The lead-out circuit 150 may lead-out the detection signal output from the transistor turned on in response to the gate pulse. The lead-out circuit 150 may lead-out the detection signal output from the pixel P in an off-set lead-out section for leading-out an off-set image and an X-ray lead-out section for leading-out a detection signal after an exposure of the X-ray.

Figure 2:
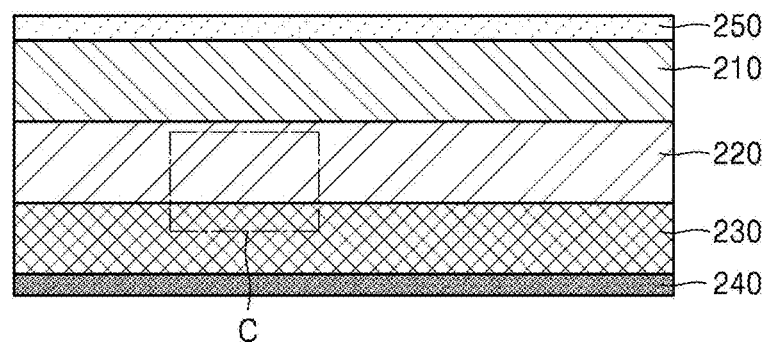
FIG. 2 illustrates, in cross-section the X-ray detector of FIG. 1.
Figure 3:
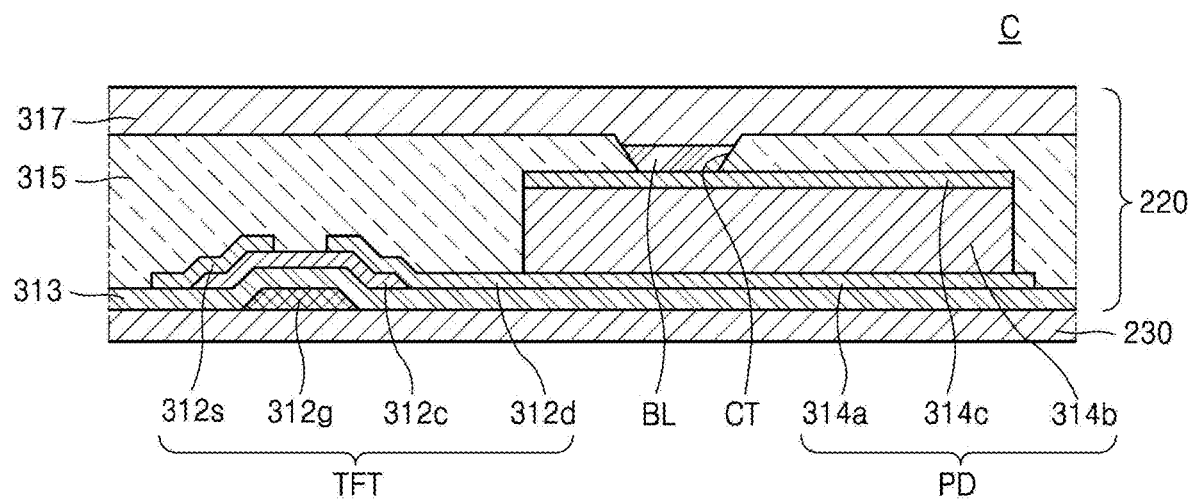
FIG. 3 illustrates a sensing layer and a protective layer of FIG. 2.

FIG. 2 illustrates, in cross-section, an X-ray detector according to certain embodiments (for example, X-ray detector 100 of FIG. 1), and FIG. 3 illustrates a sensing layer and a protective layer according to certain embodiments of this disclosure (for example, sensing layer2 220 and a protective layer 230 of FIG. 2). The area shown in detail in FIG. 3 is marked "C" in FIG. 2. As illustrated in the non-limiting examples FIGS. 2 and 3, the X-ray detector 100 may include a photoconversion layer 210 converting an X-ray into light of a different wavelength range, the sensing layer 220 arranged in the photoconversion layer 210 and including a plurality of pixels configured to convert light into an electrical signal, the protective layer 230 arranged on the sensing layer 220 and protecting the sensing layer 220 from external physical shocks, and an anti-static layer 240 preventing electrostatic charges from being introduced into the sensing layer 220.

The photoconversion layer 210 may convert the X-ray into the light of the different wavelength range, for example, a visible ray. The photoconversion layer 210 may include a scintillator or a phosphor. For example, the photoconversion layer 210 may convert the X-ray having a wavelength of dozens of nm to about 0.01 nm into green light having a wavelength of about 450 nm to about 600 nm. A thickness of the photoconversion layer 210 is about 300 μm to about 700 μm. The photoconversion layer 210 may include one of CsI and Gadox. However, the photoconversion layer 210 is not limited thereto, and may include NaI (T1), CsI (T1), CaI (Na), LiI (Eu), CaF2 (Eu), CdTe, Hg12, etc. Here, NaI is alkali metal crystal, and T1 is an impurity, added as an activator.

According to certain embodiments, an X-ray may be converted into light, for example, a visible ray, in the photoconversion layer 210, and may be incident into the sensing layer 220. The converted light may be scattered by passing through the photoconversion layer 210. Thus, the X-ray detector 100 may further include a reflection layer 250 configured to reflect the scattered light toward the sensing layer 220. The reflection layer 250 may be arranged at an upper surface of the photoconversion layer 210.

In some embodiments, sensing layer 220 may include a photodiode PD capable of receiving light and performing photoelectric conversion and a thin film transistor TFT capable of switching a charge output from the photodiode PD. In addition, the sensing layer 220 may further include a circuit unit and lines configured to control the thin film transistor TFT, etc. The photodiode PD and the thin film transistor TFT may be called as pixels P, and the sensing layer 220 may include the plurality of two-dimensionally arranged pixels P. Also, as described below, the photodiode PD and the thin film transistor TFT may be arranged in parallel in a direction perpendicular to a direction in which the X-ray is incident.

The sensing layer 220 may be arranged on the protective layer 230. The protective layer 230 may include a transparent material, and may include a flexible material to prevent external physical shocks from being transmitted to the sensing layer 220. The protective layer 230 may include a material having a less specific gravity than the glass substrate 270, light, and not easily broken, for example, a polymer material. Thus, even if shocks are applied to the X-ray detector 100, the protective layer 230 may not be broken so as to prevent damage to the sensing layer 220.

According to some embodiments, the protective layer 230 is thin, the protective layer 230 is light and may contribute to the overall thinness of the X-ray detector 100. According to other embodiments, the protective layer 230 may have sufficient thickness to support weights of the sensing layer 220 and the photoconversion layer 210, when the sensing layer 220 and the photoconversion layer 210 are manufactured. Alternatively, when the protective layer 230 is formed on a substrate, for example, a glass substrate, the protective layer 230 may have a thickness to support a weight thereof, when the protective layer 230 and the glass substrate are separated from each other. Alternatively, the protective layer 230 may make a uniform surface to form the sensing layer 220 and the photoconversion layer 210.

The protective layer 230 may include, for example, at least one of polyimide (PI), polycarbonate (PC), polyethersulfone (PES), polyethylene terephthalate (PET), polyethylenenaphthalate (PEN), polyarylate (PAR), and glass fiber reinforced plastic (FPR). A buffer layer configured to prevent penetration of impurities and planarizing a surface may be formed on an upper surface of the protective layer 230. The buffer layer is not an essential component, and may be selectively provided according to necessity.

The thin film transistor TFT in the sensing layer 220 may be formed to be adjacent to a region in which the gate lines GL and the data lines DL cross each other. The thin film transistor TFT may be turned-on in response to a gate pulse and may transmit a signal output from the photodiode PD to the data lines DL. The thin film transistor TFT may include a gate electrode 312g, a semiconductor pattern 312c, a source electrode 312s, and a drain electrode 312d. The gate electrode 312g may be formed by being branched off from the gate line GL and may transmit the gate pulse. A gate insulating layer 313 for insulation may be formed on the gate electrode 312g. The semiconductor pattern 312c may be formed on the gate insulting layer 313 to overlap the gate electrode 312g. The semiconductor pattern 312c may include a semiconductor material, such as hydride amorphous silicon or polycrystalline silicon. However, the semiconductor pattern 312c is not limited thereto and may include an oxide semiconductor.

The source electrode 312s and the drain electrode 312d may be formed to contact the semiconductor pattern 312c. The drain electrode 312d may be electrically connected to a lower portion of the photodiode PD. The source electrode 312s may be formed by being branched off from the data line DL. An ohmic contact pattern (not shown) configured to reduce a contact resistance may further be formed between the semiconductor pattern 312c and the source electrode 312s and between the semiconductor pattern 312c and the drain electrode 312d. Hereinabove, the thin film transistor TFT of an inverted staggered type has been described. However, the thin film transistor TFT is not limited to thereto, and may include a staggered type, a co-planar type, or an inverted co-planar type.

The photodiode PD may, in various embodiments, include a PIN diode. The photodiode PD may be formed on the gate insulating layer 313. The photodiode PD may include a lower electrode 314a, an upper electrode 314c, and a semiconductor unit 314b. The lower electrode 314a may be formed on the gate insulating layer 313 and electrically connected to the drain electrode 312d. The lower electrode 314a may be formed by using the same process as the drain electrode 312d and directly connected to the drain electrode 312d. However, the lower electrode 314a is not limited thereto, and may be formed by using a different process from the drain electrode 312d and formed above or below the drain electrode 312d.

The semiconductor unit 314 may be formed on the lower electrode 314a and may convert light into an electrical signal. The semiconductor unit 314b may include an N-type semiconductor layer, an intrinsic semiconductor layer, and a P-type semiconductor layer sequentially formed on the lower electrode 314a. The intrinsic semiconductor layer may be formed to be relatively thicker than the N-type semiconductor layer and the P-type semiconductor layer.

The upper electrode 314c may be formed on the semiconductor unit 314b. The upper electrode 314c may include a transparent conductive material so that light is transmitted to the semiconductor unit 314b. For example, the transparent conductive material may include one or more of ITO, IZO, ZnO, and $In_2O_3$.

A device protective layer 315 may be formed on the thin film transistor TFT, the lines, and the photodiode PD to cover the thin film transistor TFT, the lines, and the photodiode PD. The device protective layer 315 may protect devices arranged below the device protective layer 315 from an external environment. The device protective layer 315 may include a single layer or multiple layers including an inorganic insulating material or an organic insulating material. A contact hole CT may be formed in the device protective layer 315 corresponding to the photodiode PD. The photodiode PD and the bias lines BL may be electrically connected to each other via the contact hole CT.

The bias lines BL may overlap the photodiode PD and may extend in a second direction. The bias lines BL may be formed in parallel to the data lines DL. However, the bias lines BL are not limited thereto, and the bias lines BL may be formed in parallel to the gate lines GL. One or more of the bias lines BL may be branched off in a first direction crossing the second direction and may overlap the thin film transistor TFT. The bias lines BL may be electrically connected to the upper electrode 314c via the contact hole CT. The bias lines BL may receive reverse bias or forward bias from the bias supply unit 120 (refer to FIG. 2) and transmit the reverse bias or the forward bias to the photodiode PD.

An insulating layer 317 may further be formed on the device protective layer 315 to cover the bias lines BL. The insulating layer 317 may prevent penetration of impurities and secure surface planarization. The insulting layer 317 may include a single layer or multiple layers including an inorganic insulating material or an organic insulating material. The sensing layer 220 may include the protective layer 230 and the insulating layer 317 covering devices, such as the thin film transistor TFT, the photodiode PD, etc. A thickness of the sensing layer 220 is about 1 to about 3 µm. However, the thickness of the sensing layer 220 is not limited thereto. The sensing layer 220 may further include other layers in addition to the layers mentioned above.

The X-ray detector 100 may be arranged on the sensing layer 220, and may further include the anti-static layer 240 preventing an electrostatic charge from being introduced into the sensing layer 220. The anti-static layer 240 may be arranged below the protective layer 230 to contact the protective layer 230. The anti-static layer 240 may include a conductive material. For example, the anti-static layer 240 may include at least one of ITO, IZO, a metal, a conductive organic material. Also, the anti-static layer 240 may be in a ground state. The anti-static layer 240 may have a thin film shape, and a thickness thereof may be about 50 Å through about 500 Å.

The sensing layer 220 of the X-ray detector 100 may sensitively react with a small charge. For example, when pressure, vibration shocks, etc. are applied to the X-ray detector 100, a static charge may be generated. When a static charge is introduced to the sensing layer 220 from the outside, the sensing layer 220 may output an electrical signal with respect to the electrostatic charge, and thus, a malfunction of the X-ray detector 100 may occur, and an artifact may be included in an image obtained from the X-ray detector 100. The grounded anti-static layer 240 may discharge the electrostatic charge, thereby preventing the image artifact from being generated. The X-ray detector 100 of FIG. 3 may be mounted above a support frame (not shown) to secure planarization.

FIGS. 4 through 7 illustrate, in cross-section X-ray detectors 101, 102, 103, and 104 according to various embodiments.

Figure 4:
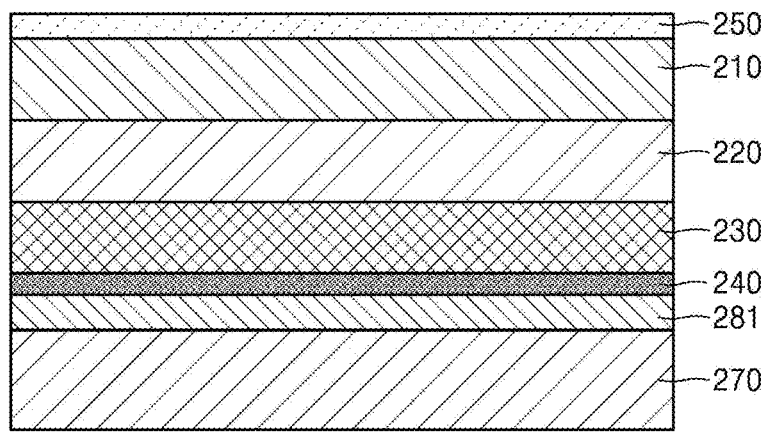
FIGS. 4 through 7 illustrate cross-sectional views of X-ray detectors according to various embodiments of this disclosure.

Comparing the non-limiting examples of FIGS. 2 and 4, the X-ray detector 101 of FIG. 4 may include the substrate 270 and may further include a first coupling layer 281 configured to couple the substrate 270 and the anti-static layer 240. The substrate 270 may include a transparent glass material comprising $SiO_2$. The substrate 270 may support the photoconversion layer 210, the sensing layer 220, the protective layer 230, and the anti-static layer 240 in a manufacturing process. FIG. 2 illustrates a state in which the substrate 270 is not separated. A thickness of the first coupling layer 281 may be about 50 µm to about 100 µm. Even if the substrate 270 including the glass material is broken due to physical shocks, the protective layer 230 may not be broken, and thus, the X-ray detector 101 may normally operate.

Figure 5:
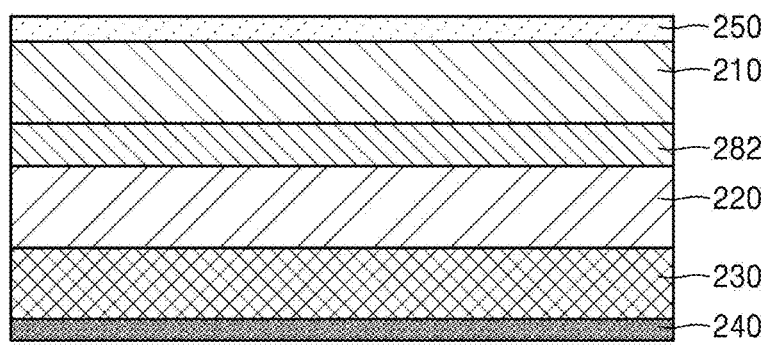

Comparing the non-limiting examples of FIGS. 2 and 5, the X-ray detector 102 of FIG. 5 may further include a second coupling layer 282 between the photoconversion layer 210 and the sensing layer 220. The second coupling layer 282 may couple the photoconversion layer 210 to the sensing layer 220. A thickness of the second coupling layer 282 may be about 50 μm to about 100 μm. That is, the sensing layer 220 of FIG. 2 may be deposited on the protective layer 230, and the X-ray detector 102 of FIG. 5 may be manufactured by coupling the photoconversion layer 210 to the sensing layer 220.

Figure 6:
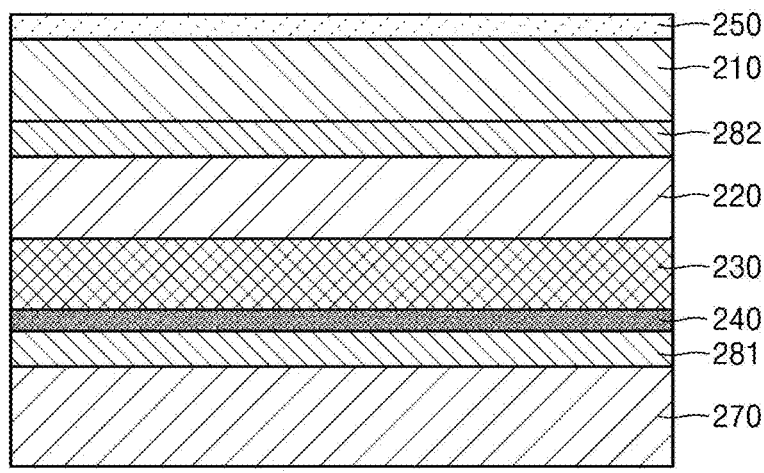

Comparing the non-limiting examples of FIGS. 2 and 6, the X-ray detector 103 of FIG. 6 may include the substrate 270, and may further include the first coupling layer 281 configured to couple the substrate 270 and the anti-static layer 240 and the second coupling layer 282 configured to couple the photoconversion layer 210 and the sensing layer 220. The X-ray detector 103 of FIG. 6 may be manufactured by separately manufacturing the photoconversion layer 210 in a state in which the anti-static layer 240, the protective layer 230, and the sensing layer 220 are not separated, as illustrated in FIG. 4, and coupling the photoconversion layer 210 to the sensing layer 220 via the second coupling layer 282.

Figure 7:
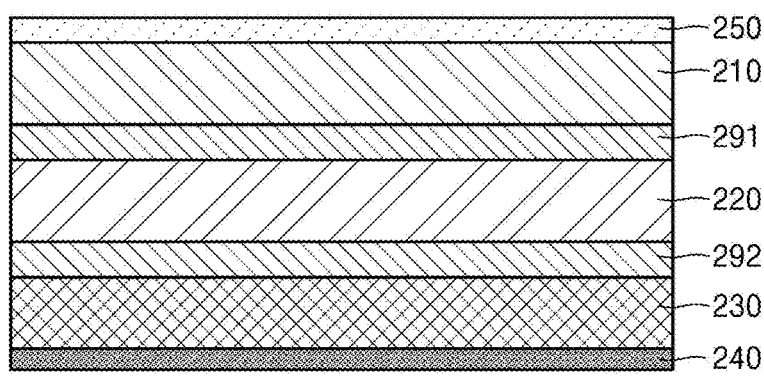

Comparing the non-limiting examples of FIGS. 2 and 7, the X-ray detector 104 of FIG. 7 may further include a first barrier layer 291 arranged between the photoconversion layer 210 and the sensing layer 220 and preventing water penetration into the sensing layer 220, and a second barrier layer 292 arranged between the sensing layer 220 and the protective layer 230 and preventing water penetration into the sensing layer 220. The first and second barrier layers 291 and 292 may include an inorganic material, such as SiOx, SiNx, SiNO, AlO, and AlON, an organic material, such as acryl and polyimide, or a stack of an organic material and an inorganic material.

The photodiode PD included in the sensing layer 220 may be very vulnerable to water. Thus, the first barrier layer 291 may be arranged above the sensing layer 220 and the second barrier layer 292 may be arranged below the sensing layer 229 so that the first and second barrier layers 291 and 292 may prevent oxygen and water from being introduced into the sensing layer 220. FIG. 7 illustrates both of the first and second barrier layers 291 and 292. However, the present disclosure is not limited thereto. The X-ray detector 104 may include any one of the first and second barrier layers 291 and 292. Also, at least one of the first and second barrier layers 291 and 292 may be included in the X-ray detectors 101, 102, and 103 illustrated in FIGS. 4 through 6.

Figure 8A:
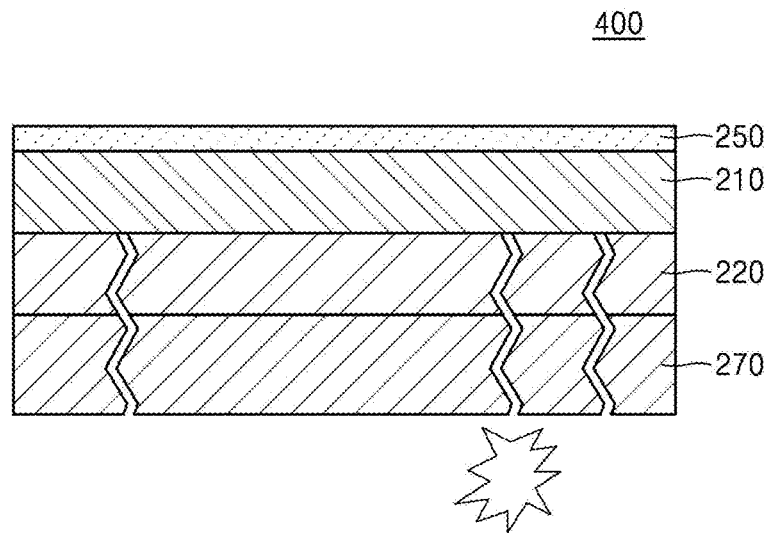
FIGS. 8A and 8B illustrate the effects of external shocks applied to an X-ray detector not including a protective layer according to certain embodiments of this disclosure and the effect of external shocks applied to an X-ray detector including the protective layer according to certain embodiments.
Figure 8B:
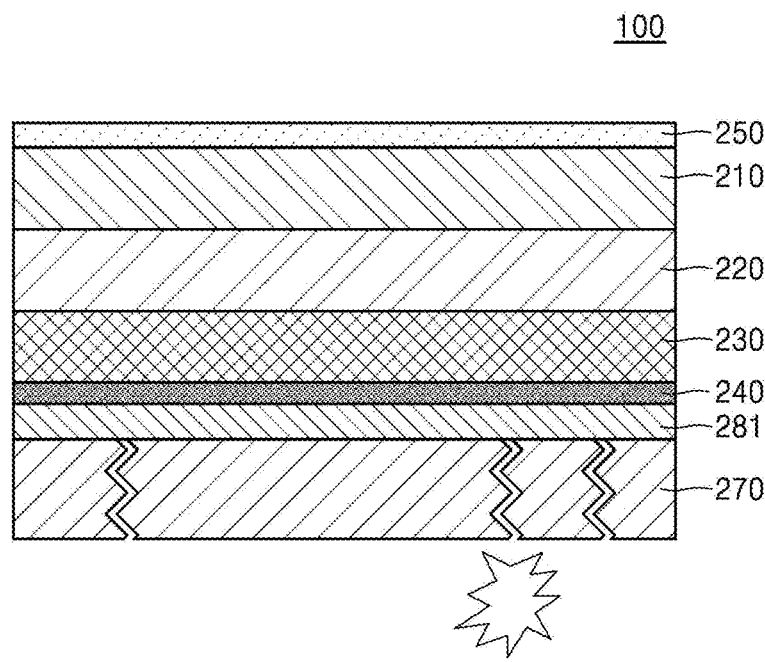

FIGS. 8A and 8B illustrate the effects of external shocks applied to an X-ray detector 400 not including a protective layer and to an X-ray detector 100 according to various embodiments, which include the protective layer 230. As illustrated in FIG. 8A, the sensing layer 220 and the photoconversion layer 210 may be arranged on the substrate 270 including a glass material. The substrate 270 can be vulnerable to physical shocks, and thus, may be easily broken. When the substrate 270 is broken, the sensing layer 220 may be fractured. Accordingly, the X-ray detector 100 may not normally operate. However, as illustrated in the non-limiting example of FIG. 8B, when the anti-static layer 240 and the protective layer 230 are arranged on the substrate 270, and the sensing layer 220 and the photoconversion layer 210 are arranged on the anti-static layer 240 and the protective layer 230, even if the glass substrate 270 is broken, the protective layer 230 may not be broken, so that the sensing layer 220 may not be fractured. Accordingly, the X-ray detector 100 may continue to operate normally.

FIGS. 9 through 15 are reference views illustrating aspects of a method of manufacturing the X-ray detector 100 of FIG. 2 according embodiments of this disclosure.

Figure 9:
FIGS. 9 through 15 illustrate aspects of a method of manufacturing an X-ray detector according to certain embodiments.

As illustrated in the non-limiting example of FIG. 9, substrate 270 may, in certain embodiments, be provided. The substrate 270 may include a transparent glass material mainly including SiO2. The substrate 270 is not necessarily limited thereto, and may include a transparent plastic material.

Figure 10:
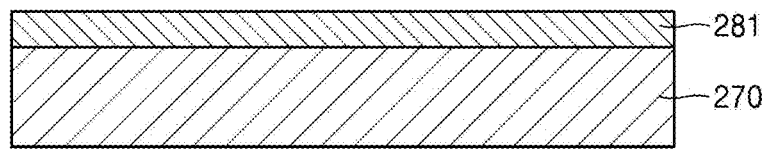
Figure 11:
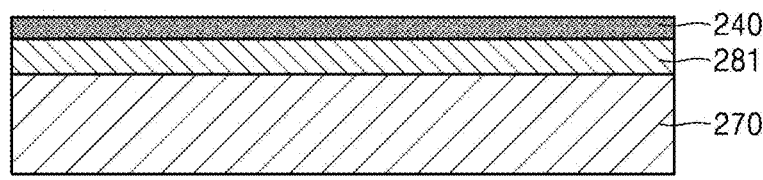

As illustrated in the non-limiting example of FIG. 10, the first coupling layer 281 may be formed on the substrate 270, and as illustrated in FIG. 11, in some embodiments, the anti-static layer 240 may be formed. The anti-static layer 240 may include a conductive material, for example, at least one of ITO, IZO, a metal, and a conductive organic material. The anti-static layer 240 may be formed by a thin film deposition process, such as sputtering. The anti-static layer 240 may be formed by using the deposition process, and thus, the process may be simple and the anti-static layer 240 may be easily manufactured. Alternatively, a conductive film may be coupled to the first coupling layer 281. The anti-static layer 240 may be grounded. Thus, even if shocks, pressures, vibrations, etc. are applied to the X-ray detector 100 when the X-ray detector 100 obtains an image, electrostatic charges generated due to the shocks, pressures, vibrations, etc. may be discharged via the anti-static layer 240. Image noise may be removed.

Figure 12:
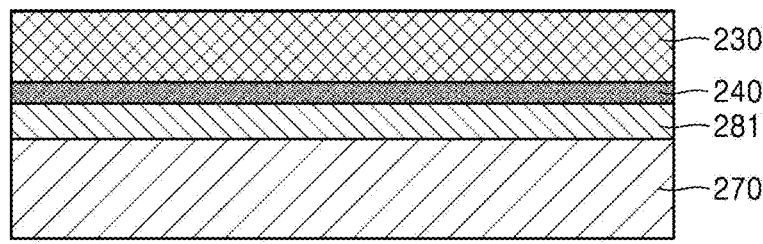

As illustrated in FIG. 12, the protective layer 230 may, according to various embodiments, be formed on the anti-static layer 240. The protective layer 230 may include a transparent material, and may include a material having sufficient flexibility to prevent external shocks from being transmitted to the sensing layer 220. The protective layer 230 may include, for example, at least one of PI, PC, PES, PET, PEN, PAR, and FPR. The protective layer 230 may be formed by a coating process whereby a flexibility solution is spread on the anti-static layer 240 and the flexibility solution is hardened at a high temperature. Alternatively, the protective layer 230 may be formed by a printing method after making a flexible material as a roll-to-roll shape. Alternatively, the protective layer 230 having a film shape may be coupled to the anti-static layer 240 to form the protective layer 230.

Figure 13:
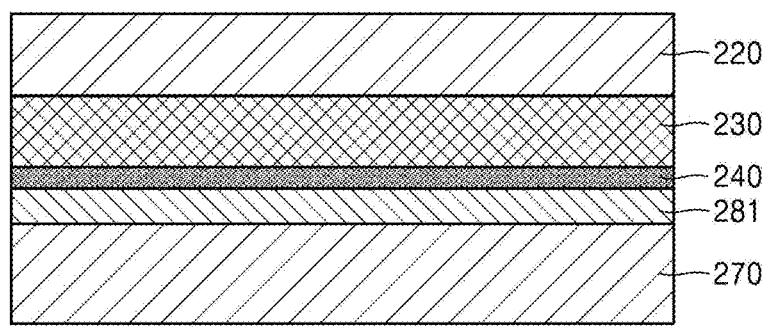
Figure 14:
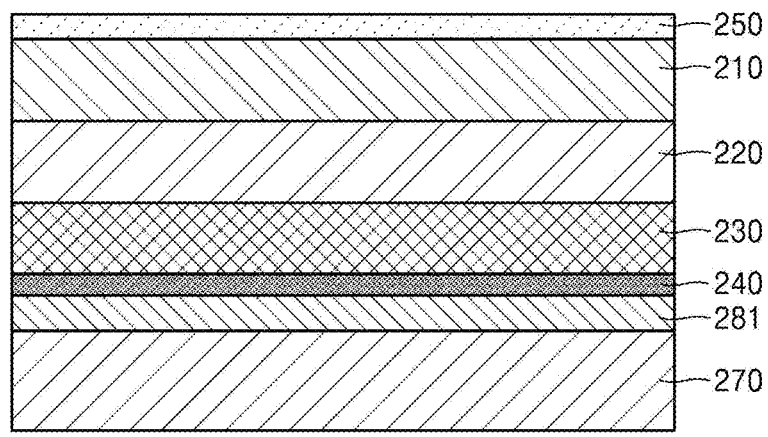

Also, as illustrated in FIGS. 13 and 14, the sensing layer 220, the photoconversion layer 210, and the reflection layer 250 may, according to various embodiments be sequentially formed on the protective layer 230. The sensing layer 220, the photoconversion layer 210, and the reflection layer 250 may be formed by using the method of manufacturing the X-ray detector 100, and thus, detailed descriptions thereof will be omitted. The non-limiting example of FIG. 13 illustrates that the photoconversion layer 210 may be directly deposited on the sensing layer 220. However, the present disclosure is not limited thereto. The photoconversion layer 210 may be formed on the additional substrate 270, and the photoconversion layer 210 may be coupled to the sensing layer 220 by using the second coupling layer 282. The X-ray detector 100 illustrated in FIG. 14 may be used.

Figure 15:
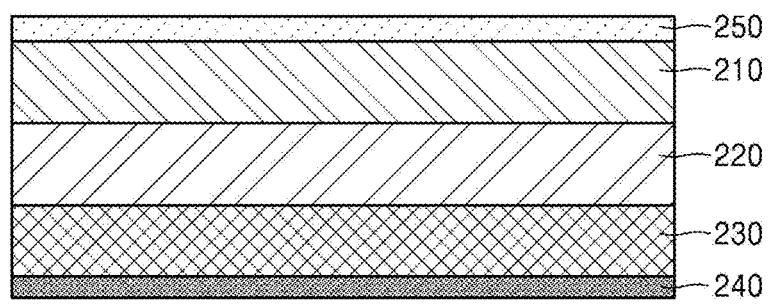

Alternatively, as illustrated in the non-limiting example of FIG. 15, the first coupling layer 281 and the substrate 270 may be removed from the anti-static layer 240. For example, the first coupling layer 281 and the substrate 270 may be removed from the anti-static layer 240 by deriving reaction from the first coupling layer 281 by using a laser beam. Although not shown in FIGS. 9 through 15, the first barrier layer 291 may, according to some embodiments, be formed on the sensing layer 220 before the photoconversion layer 210 is formed. The second barrier layer 292 may be formed on the protective layer 230 before the sensing layer 220 is formed.

Figure 16:
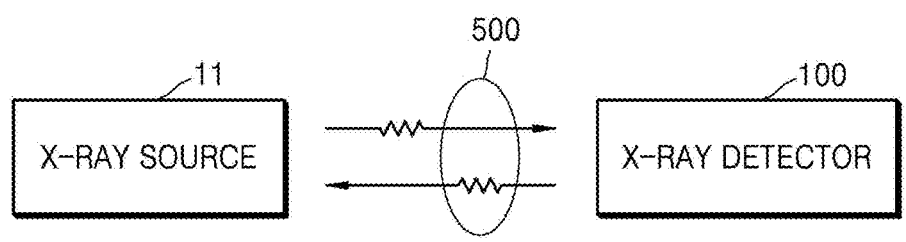
FIG. 16 illustrates, in block diagram format, an X-ray photographing apparatus according to certain embodiments.
Figure 17:
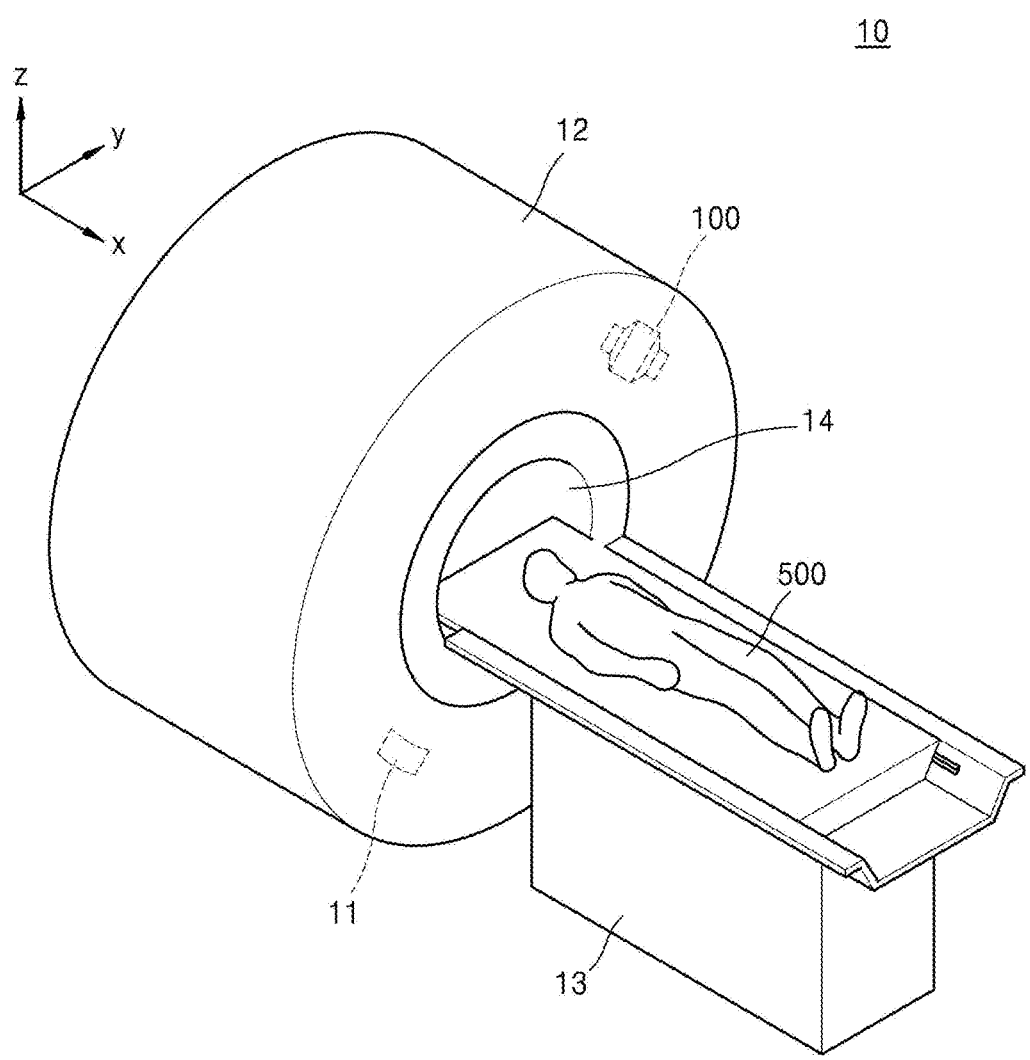
FIG. 17 illustrates an exterior portion of an X-ray photographing apparatus according to various embodiments.

Embodiments of the X-ray detector 100 described above may be included in an X-ray photographing apparatus, along with the X-ray source 11 configured to generate X-rays. FIG. 16 illustrates in block diagram format, an X-ray photographing apparatus 10 according to certain embodiments and FIG. 17 illustrates a partial exterior view of an X-ray photographing apparatus 10 according to various embodiments. As illustrated in the non-limiting examples of FIGS. 16 and 17, the X-ray photographing apparatus 10 may include the X-ray source 11 configured to scan the X-rays, and the X-ray detector 100 configured to detect an X-ray which penetrates into an object, form among the X-rays scanned by the X-ray source 11. The X-ray source 11 may include at least one X-ray generator (not shown) configured to generate an X-ray. When the X-ray generator includes a plurality of X-ray generators, the plurality of X-ray generators may be arranged one-dimensionally or two-dimensionally.

The plurality of X-ray generators may, in certain embodiments, operate separately to generate an X-ray, or one or more of the plurality of X-ray generators may operate to generate an X-ray toward an object 500. Furthermore, one or more of the plurality of X-ray generators may simultaneously operate or sequentially operate. The X-ray detector 100 described above is applied to the X-ray photographing apparatus 10 according to the present embodiment, and thus, its detailed description will not be given.

The X-ray photographing apparatus 10 according to certain embodiments of this disclosure may further include a gantry 12 and a check-out stand 13. An opening 14 having a cylindrical shape may be provided at a center of the gantry 12, so that the object 500 may be inserted into the opening 14. Also, the X-ray source 11 configured to scan the X-rays and the X-ray detector 100 configured to detect the X-ray which penetrates into the object 500 may be arranged in the gantry 12. The X-ray source 11 may be arranged to face the X-ray detector 100, with the object 500 at a center of a certain area along a circumference of the opening 14 of the gantry 12 For example, the X-ray source 11 and the X-ray detector 100 may be provided in the gantry 12 as a structure in which an X-ray is vertically incident.

The gantry 12 may, in some embodiments, rotate along a circumference of the object 500 at 360 degrees or a certain angle via a gantry driver (not shown) so that an image is captured by the X-ray source 11 and the X-ray detector 100 at various angles. Also, the gantry driver may perform a backward or a forward horizontal movement, that is, an X-axis movement, so that a photographing portion of the object 500 lying on the check-out stand 13 is located at an inner central portion of the gantry 12. The gantry driver may be provided in the gantry 12 or may be arranged outside the gantry 12.

According to some embodiments, check-out stand 13 may be provided as a type of bed having a certain width, on which a patient may lie down and may be fixed, and an check-out stand driver (not shown) configured to move the check-out stand 13 to the opening 14 provided at the central portion of the gantry 12 may be provided at a certain area of the check-out stand 13. The check-out stand 13 may perform a backward or a forward horizontal movement so that a photographing part of the patient is located at the inner central portion of the gantry 12, via the check-out stand driver. The check-out stand driver may obtain a vivid image by moving the check-out stand 13 in an up and down direction, that is, a z-axis direction, or in a left and right direction, that is, a y-axis direction, based on a body size and the photographing part of the patient. FIG. 17 illustrates a computed tomography (CT) apparatus, as a non-limiting example of the X-ray photographing apparatus 10 according to certain embodiments. However, the X-ray photographing apparatus 10 is not limited thereto. The X-ray photographing apparatus 10 may include all apparatus having an X-ray as a source.

In addition, the X-ray photographing apparatus 10 may further include a signal processor configured to obtain an image by using a result of detection of the X-ray detector 100, a display configured to display the image, an input unit configured to receive a user command, and a controller configured to control general operations of the X-ray photographing apparatus 10. However, these components are well known, and thus, their descriptions will be omitted.

Figure 18:
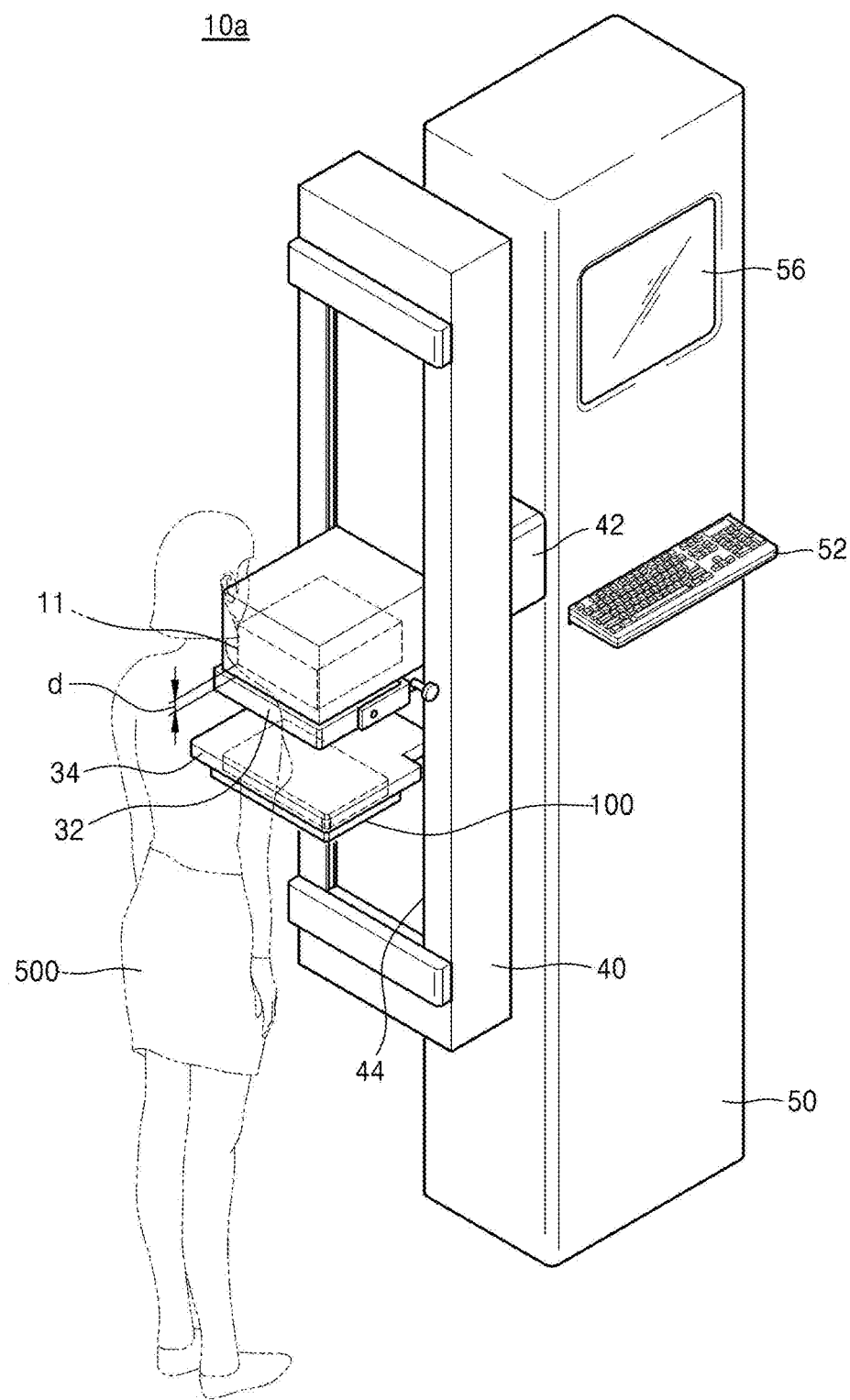
FIG. 18 illustrates an exterior portion of an X-ray photographing apparatus according to some embodiments.

FIG. 18 illustrates an exterior view of an X-ray photographing apparatus 10*a* according to some embodiments. The X-ray photographing apparatus 10*a* illustrated in FIG. 18 is a mammography apparatus configured to photograph the breast. However, X-ray photographing apparatuses according to the present disclosure are not limited to the mammography apparatus, and may include all X-ray photographing apparatuses configured to generate X-rays after contacting an object.

As illustrated in the non-limiting example of FIG. 18, the X-ray photographing apparatus 10*a* may include an X-ray generator 11 configured to generate X-rays, the X-ray detector 100 configured to detect an X-ray which penetrates into the object 500, and panels 32 and 34 configured to be capable of contacting the object 500. Also, the X-ray photographing apparatus 10*a* may further include a gantry 40 configured to support the X-ray generator 11, the X-ray detector 100, and the panels 32 and 34, and may further include a body 50 configured to support the gantry 40.

The body 50 may include a user input unit 52 via which a user command for operating a medical device may be input, a signal processor (not shown) configured to generate an image corresponding to a penetrating X-ray, a display 56 configured to display the generated image, and a controller (not shown) configured to control general operations of the X-ray photographing apparatus 10*a*. The user input unit 52, the signal processor, the display 56, and the controller do not necessarily have to be provided in the body 50, and may be implemented as external devices capable of communicating with the X-ray photographing apparatus 10*a* via wires or wirelessly.

Also, the gantry 40 may, in some embodiments, be fixed to the body 50 via a gantry driver 42. The gantry 40 may be arranged at a side surface of the body 50 in a longitudinal direction, and the gantry driver 42 may rotate the gantry 40 at 360 degrees or a certain angle. Also, the gantry driver 42 may drive the gantry 40 to ascend toward the body 50 in a longitudinal direction. Thus, the gantry 40 may move in an up and down direction in the longitudinal direction of the body 50 via the gantry driver 42 so as to have an adjusted height with respect to the object 500, and the gantry 40 may be rotated by the gantry driver 42.

Also, the panels 32 and 34 capable of contacting the object 500, for example, the first and second panels 32 and 34, may be arranged at a front surface of the gantry 40. The first and second panels 32 and 34 may move in an up and down direction via a guide groove 44 provided at the front surface of the gantry 40 in a longitudinal direction. Thus, when the object 500, for example, the breast of a patient, is arranged between the first and second panels 32 and 34, at least one of the first and second panels 32 and 34 may press and compress the object 500. For example, when the second panel 34 is moved in an up and down direction to mount the object 500 on an upper surface of the second panel 34 and the first panel 32 is moved in a down direction, the object 500 may be pressed and compressed.

The X-ray generator 11 configured to generate X-rays may be provided above the first panel 32. The X-ray generator 11 may be moved to be apart or near from or to the object 500 by maintaining a certain distance d from the first panel 32. For example, the X-ray generator 11 may be integrated with the first panel 32 and may move along the guide groove 44 together with the first panel 32.

Since, in certain embodiments, the X-ray generator 11 generates X-rays toward the object 500 in the state in which the first panel 32 presses the object 500, a distance between the X-ray generator 11 and the object 500 may be minimized. For example, the distance between the X-ray generator 11 and the object 500 may be within about 10 cm. Thus, it may be possible to prevent X-rays being emitted toward other areas than the object 500, so as to minimize exposure to the X-rays. In order to minimize the distance between the X-ray generator 11 and the object 500, the X-ray generator 11 may be arranged to contact an upper surface of the object 500. Also, the X-ray generator 11 may include a plurality of X-ray generating units 300.

Also, the X-ray detector 100 configured to detect an X-ray which penetrates into the object 500 may be provided below the second panel 34. The X-ray detector 100 may move to be apart or near from or to the object 500 by maintaining a certain distance from the second panel 34. For example, the X-ray detector 100 may be integrated with the second panel 34 and move along the guide groove 44 together with the second panel 34.

Since, in certain embodiments, the X-ray detector 100 detects the X-ray which penetrates into the object 500 in a state in which the object 500 is mounted in the second panel 34, a distance between the X-ray detector 100 and the object 500 may be minimized. Thus, detection of the X-ray may become more precise. In order to minimize the distance between the X-ray detector 100 and the object 500, the X-ray detector 100 may be arranged to contact a lower surface of the second panel 34. Also, the X-ray detector 100 may be detachably attached to the second panel 34, and may be frequently replaced. The X-ray detector 100 according to the present disclosure has high durability. Image noise may be reduced via the structure of the X-ray detector 100.

The X-ray photographing apparatus 10 and 10a illustrated in FIGS. 17 and 18 are only illustrative examples. The X-ray detector 100 described hereinabove may be applied to various types of X-ray photographing apparatus.

It should be understood that embodiments described herein should be considered in a descriptive sense only and not for purposes of limitation. Descriptions of features or aspects within each embodiment should typically be considered as available for other similar features or aspects in other embodiments.

Although the present disclosure has been described with various embodiments, various changes and modifications may be suggested to one skilled in the art. It is intended that the present disclosure encompass such changes and modifications as fall within the scope of the appended claims.

What is claimed is:

1. An X-ray detector comprising:
   a photoconversion layer configured to convert an X-ray into light having a wavelength range that is different from a wavelength range of the X-ray;
   a sensing layer arranged on the photoconversion layer and comprising a plurality of pixels configured to output the light as an electrical signal;
   a flexible protective layer arranged on the sensing layer and protecting the sensing layer from physical shocks;
   a barrier layer formed of a material different from a material of the flexible protective layer, arranged between the sensing layer and the flexible protective layer and preventing water from penetrating into the sensing layer; and
   an anti-static layer in contact with the flexible protective layer and preventing an electrostatic charge from being introduced into the sensing layer,
   wherein the photoconversion layer, the sensing layer, the barrier layer, the flexible protective layer and the anti-static layer are sequentially arranged in a direction in which the X-ray is incident.

2. The X-ray detector of claim 1, wherein each of the plurality of pixels comprises a photodiode and a transistor arranged in parallel in a direction perpendicular to a direction in which the X-ray is incident.

3. The X-ray detector of claim 1, wherein the anti-static layer comprises a conductive material.

4. The X-ray detector of claim 1, wherein a thickness of the anti-static layer ranges from approximately 50 Å to 500 Å.

5. The X-ray detector of claim 1, wherein the anti-static layer is grounded.

6. The X-ray detector of claim 1, further comprising:
   a second barrier layer arranged between the photoconversion layer and the sensing layer.

7. The X-ray detector of claim 1, further comprising:
   a substrate arranged on the flexible protective layer and supporting the flexible protective layer.

8. The X-ray detector of claim 7, further comprising:
   a first coupling layer configured to couple the substrate and the flexible protective layer together.

9. The X-ray detector of claim 1, further comprising:
   a second coupling layer configured to couple the photoconversion layer and the sensing layer together.

10. The X-ray detector of claim 1, wherein the plurality of pixels are two-dimensionally arranged.

11. A method of manufacturing an X-ray detector, the method comprising:
   forming a flexible material layer on an anti-static material layer;
   forming, on the flexible material layer, a sensing layer comprising a plurality of pixels configured to convert light into an electrical signal;
   forming, on the sensing layer, a photoconversion layer configured to convert an X-ray into the light; and
   forming a barrier layer of a material different from a material of the flexible protective layer, between the sensing layer and the flexible material layer, configured to prevent water from penetrating into the sensing layer,
   wherein each of the plurality of pixels comprises a photodiode and a transistor arranged in parallel on the flexible material layer,
   wherein the photoconversion layer, the sensing layer, the barrier layer, the flexible material layer and the anti-static material layer are sequentially arranged in a direction in which the X-ray is incident.

12. The method of claim 11, further comprising:
   forming a coupling layer on a substrate; and
   forming the anti-static material layer on the coupling layer.

13. The method of claim 11, wherein the anti-static material layer is grounded.

14. The method of claim 11, wherein the flexible material layer is formed by a coating process.

* * * * *